United States Patent
Le Grand

(10) Patent No.: US 8,219,372 B1
(45) Date of Patent: Jul. 10, 2012

(54) COMPUTER-READABLE MEDIUM, METHOD AND COMPUTING DEVICE FOR N-BODY COMPUTATIONS USING PARALLEL COMPUTATION SYSTEMS

(75) Inventor: Scott Le Grand, Soquel, CA (US)

(73) Assignee: NVIDIA Corporation, Santa Clara, CA (US)

( * ) Notice: Subject to any disclaimer, the term of this patent is extended or adjusted under 35 U.S.C. 154(b) by 720 days.

(21) Appl. No.: 12/340,480

(22) Filed: Dec. 19, 2008

Related U.S. Application Data

(60) Provisional application No. 61/043,700, filed on Apr. 9, 2008, provisional application No. 61/022,502, filed on Jan. 21, 2008.

(51) Int. Cl.
*G06G 7/58* (2006.01)
*G06F 7/60* (2006.01)
*G06F 17/00* (2006.01)
*G01N 33/48* (2006.01)

(52) U.S. Cl. ............... 703/11; 700/90; 702/19; 702/20; 703/2

(58) Field of Classification Search .................. None
See application file for complete search history.

(56) References Cited

FOREIGN PATENT DOCUMENTS

| WO | WO 2008/127610 | 10/2008 |
|----|----------------|---------|
| WO | WO 2008/127622 | 10/2008 |
| WO | WO 2008/127623 | 10/2008 |

OTHER PUBLICATIONS

Moss, et al. "Toward Acceleration of RSA Using 3D Graphics Hardware," LNCS 4887, Dec. 2007, pp. 369-388.
Eggers, et al. "Simultaneous Multithreading: A Platform for Next-Generation Processors," IEEE Micro, vol. 17, No. 5, pp. 12-19, Sep./Oct. 1997.

*Primary Examiner* — Shubo Zhou
(74) *Attorney, Agent, or Firm* — Patterson & Sheridan, LLP

(57) ABSTRACT

One embodiment of the present invention sets forth a technique for efficiently performing N-body computations using parallel computation systems. The technique involves a first processing step whereby a force matrix is partitioned into tiles, which are assigned to a one or more thread groups for processing. An off-diagonal tile may be aligned to include no diagonal cells, while an on-diagonal tile includes diagonal cells. One approach for computing either type of tile involves assigning each row from a tile to a thread within a thread group. Each thread operates on an offset pattern to avoid access conflicts to a shared memory. A net force for each atom within an N-body system is then computed by efficiently adding constituent forces stored within the force matrix using reduction operations on the force matrix.

21 Claims, 16 Drawing Sheets

|   | 1 | 2 | 3 | 4 | 5 | 6 | 7 | 8 |
|---|---|---|---|---|---|---|---|---|
| 1 | F(1,1) | F(2,1) | F(3,1) | F(4,1) | F(5,1) | F(6,1) | F(7,1) | F(8,1) |
| 2 | F(1,2) | F(2,2) | F(3,2) | F(4,2) | F(5,2) | F(6,2) | F(7,2) | F(8,2) |
| 3 | F(1,3) | F(2,3) | F(3,3) | F(4,3) | F(5,3) | F(6,3) | F(7,3) | F(8,3) |
| 4 | F(1,4) | F(2,4) | F(3,4) | F(4,4) | F(5,4) | F(6,4) | F(7,4) | F(8,4) |
| 5 | F(1,5) | F(2,5) | F(3,5) | F(4,5) | F(5,5) | F(6,5) | F(7,5) | F(8,5) |
| 6 | F(1,6) | F(2,6) | F(3,6) | F(4,6) | F(5,6) | F(6,6) | F(7,6) | F(8,6) |
| 7 | F(1,7) | F(2,7) | F(3,7) | F(4,7) | F(5,7) | F(6,7) | F(7,7) | F(8,7) |
| 8 | F(1,8) | F(2,8) | F(3,8) | F(4,8) | F(5,8) | F(6,8) | F(7,8) | F(8,8) |

Figure 5C

COMPUTER-READABLE MEDIUM, METHOD AND COMPUTING DEVICE FOR N-BODY COMPUTATIONS USING PARALLEL COMPUTATION SYSTEMS

CROSS-REFERENCE TO RELATED APPLICATIONS

The present application claims the priority benefit of the U.S. Provisional Application titled, "N-BODY COMPUTATIONS USING PARALLEL COMPUTATION SYSTEMS," filed on Apr. 9, 2008 and having Ser. No. 61/043,700, and also claims the priority benefit of the U.S. Provisional Application titled, "IMPROVED N-BODY SIMULATION METHOD FOR SMALL N," filed on Jan. 21, 2008 and having Ser. No. 61/022,502. The subject matter of these related applications is hereby incorporated herein by reference.

BACKGROUND OF THE INVENTION

1. Field of the Invention

The present invention generally relates to n-body computations and more specifically to n-body computations using parallel computation systems.

2. Description of the Related Art

N-body systems are commonly used to simulate and model behaviors of interacting objects in complex systems. High-level behaviors for an N-body system may be simulated via N-body computations, which reproduce behaviors of individual bodies within the system. For example, attractive and repulsive forces, atomic masses, and atomic distances can be used to provide components of a model for simulating behaviors of a molecule comprising an N-body system of atoms.

Certain N-body computations proceed as a sequence of time steps, where state information for each time step is computed for an N-body system. The state information may include three-dimensional location and force information for each body within the N-body system. During each time step, a set of interactions is computed between each body within the system and other bodies within the system. The interactions are conventionally represented as an interaction matrix that includes a cell for each possible interaction. One type of interaction between bodies within the N-body system is force, and a force matrix may be used to represent individual forces between each body in the N-body system. For example, an N-by-N force matrix $F(i,j)$ may be used to represent inter-atomic forces between N atoms, and each cell within the force matrix $F(i,j)$ represents an individual inter-atomic force between atom i and atom j.

Because many useful N-body systems include a large number of bodies and extremely small simulation time steps, N-body simulation systems can be computationally very intensive and therefore potentially good candidates for execution on parallel computation platforms. One approach to partitioning an N-body simulation for execution on a parallel computation platform, such a graphics processing unit, involves dividing up the force matrix F into groups, such that each group is a sub-matrix of the force matrix. In each group, a number of rows for the sub-matrix may be determined by a characteristic number of threads configurable to execute together as one computational entity. A number of columns for the sub-matrix may be determined by an amount of data that can be read and stored efficiently in memory associated with the computational entity, such as a local register file. For each body within the group, one or more threads associated with the computational entity compute individual forces from the given body to each other body within the N-body system.

Parallel computation platforms conventionally embody certain limitations with respect to threads accessing one or more tiers of memory. For example, two different threads may be able to simultaneously access two different blocks within a memory subsystem if the memory blocks are not aligned, but the threads may experience lower performance when accessing two aligned memory blocks because the aligned accesses result in access conflicts. When parallel threads generate access conflict conditions, the each access commonly needs to be executed sequentially rather than in parallel (with other access requests), leading to reduced efficiency and lower overall performance.

One problem in existing N-body simulation methodologies with respect to parallel computation platforms is that common access patterns to data within the force matrix result in access conflicts, leading to lower overall efficiency. In other words, existing methodologies do not fully utilize processing throughput from the parallel computation platform.

Accordingly, what is needed in the art is a more efficient N-body simulation methodology for parallel computation platforms.

SUMMARY OF THE INVENTION

One embodiment of the present invention sets forth a computer-implemented method for computing net forces associated with a plurality of atoms in a protein-folding model. The method includes the steps of partitioning a force matrix into a plurality of tiles, where values of non-diagonal cells in the force matrix represent inter-atom forces between different atoms in a protein, and each tile includes a portion of the cells comprising the force matrix, launching a first set of thread groups to compute values for cells in each tile in the plurality of tiles, wherein the value of each cell in a tile is based on one or more properties associated with either one atom or two different atoms in the protein, and saving the computed values for the cells in each tile in a first memory space representing the force matrix. The method also includes the steps of launching a second set of thread groups to reduce the computed values for the cells in each tile stored in the first memory space to produce a net force value for each atom represented in the force matrix, and saving the net force value for each atom in a second memory space.

Other embodiments of the present invention include computer-implemented methods for computing inter-atom forces between atoms in a protein and for computing net forces on atoms in a protein.

Yet other embodiments of the present invention include computer-readable media that include instructions that, when executed, cause a processor to implement these methods or one or more variations of these methods and computing devices configured to implement these methods or one or more variations of these methods.

One advantage of the disclosed methods is the improved computational efficiency gained through more efficient memory access patterns and more efficiency use of computing resources within a parallel processing unit.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 5C is an exemplary partitioning of the force matrix for assignment to thread groups within one or more PPUs of FIG. 2, according to one embodiment of the present invention;

DETAILED DESCRIPTION

In the following description, numerous specific details are set forth to provide a more thorough understanding of the present invention. However, it will be apparent to one of skill in the art that the present invention may be practiced without one or more of these specific details. In other instances, well-known features have not been described in order to avoid obscuring the present invention.

System Overview

Figure 1:
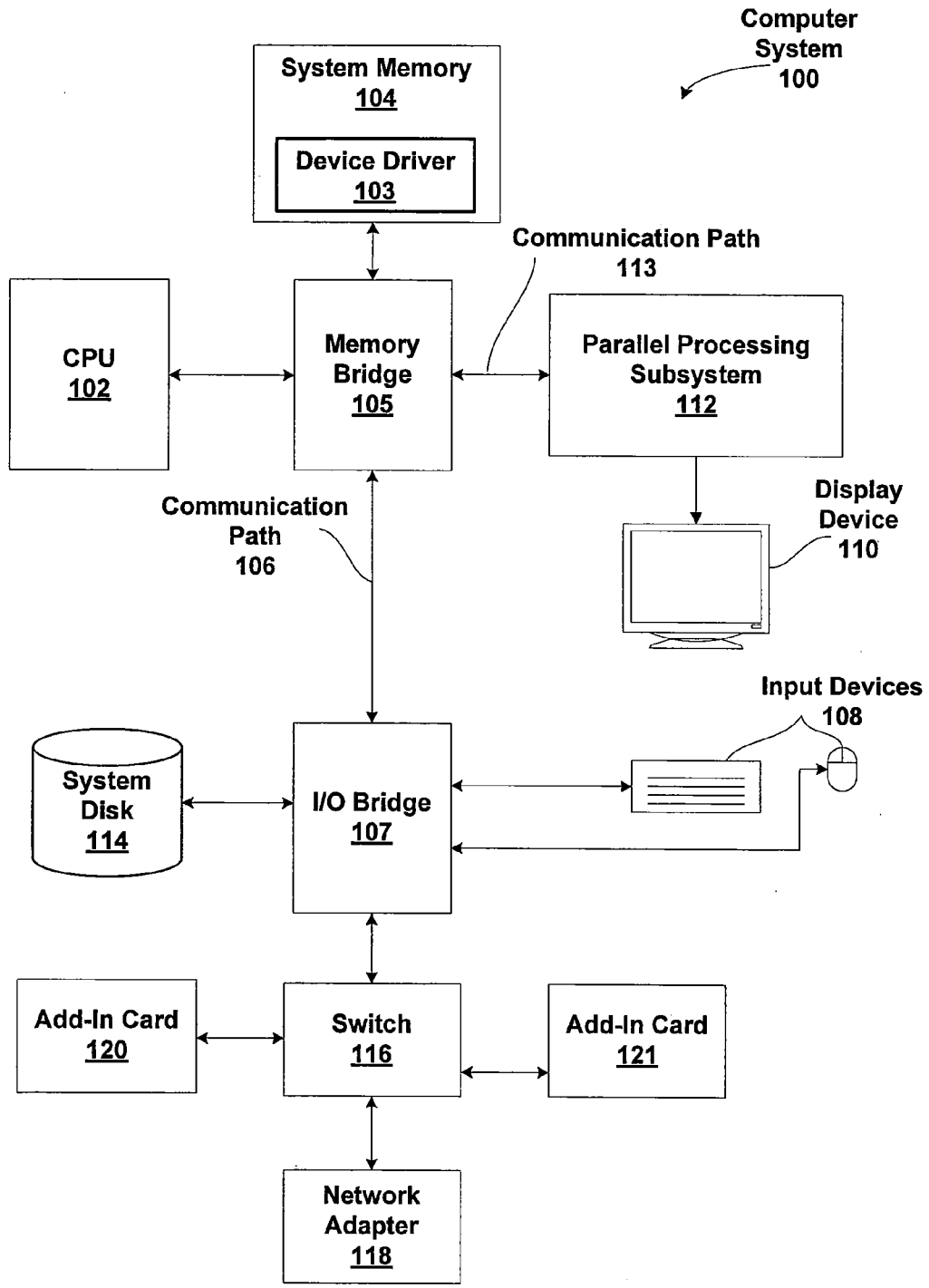
FIG. 1 is a block diagram illustrating a computer system configured to implement one or more aspects of the present invention.

FIG. 1 is a block diagram illustrating a computer system 100 configured to implement one or more aspects of the present invention. Computer system 100 includes a central processing unit (CPU) 102 and a system memory 104 communicating via a bus path that may include a memory bridge 105. Memory bridge 105, which may be, e.g., a Northbridge chip, is connected via a bus or other communication path 106 (e.g., a HyperTransport link) to an I/O (input/output) bridge 107. I/O bridge 107, which may be, e.g., a Southbridge chip, receives user input from one or more user input devices 108 (e.g., keyboard, mouse) and forwards the input to CPU 102 via path 106 and memory bridge 105. A parallel processing subsystem 112 is coupled to memory bridge 105 via a bus or other communication path 113 (e.g., a PCI Express, Accelerated Graphics Port, or HyperTransport link); in one embodiment parallel processing subsystem 112 is a graphics subsystem that delivers pixels to a display device 110 (e.g., a conventional CRT or LCD based monitor). A system disk 114 is also connected to I/O bridge 107. A switch 116 provides connections between I/O bridge 107 and other components such as a network adapter 118 and various add-in cards 120 and 121. Other components (not explicitly shown), including USB or other port connections, CD drives, DVD drives, film recording devices, and the like, may also be connected to I/O bridge 107. Communication paths interconnecting the various components in FIG. 1 may be implemented using any suitable protocols, such as PCI (Peripheral Component Interconnect), PCI Express (PCI-E), AGP (Accelerated Graphics Port), HyperTransport, or any other bus or point-to-point communication protocol(s), and connections between different devices may use different protocols as is known in the art.

In one embodiment, the parallel processing subsystem 112 incorporates circuitry optimized for graphics and video processing, including, for example, video output circuitry, and constitutes a graphics processing unit (GPU). In another embodiment, the parallel processing subsystem 112 incorporates circuitry optimized for general purpose processing, while preserving the underlying computational architecture, described in greater detail herein. In yet another embodiment, the parallel processing subsystem 112 may be integrated with one or more other system elements, such as the memory bridge 105, CPU 102, and I/O bridge 107 to form a system on chip (SoC).

It will be appreciated that the system shown herein is illustrative and that variations and modifications are possible. The connection topology, including the number and arrangement of bridges, may be modified as desired. For instance, in some embodiments, system memory 104 is connected to CPU 102 directly rather than through a bridge, and other devices communicate with system memory 104 via memory bridge 105 and CPU 102. In other alternative topologies, parallel processing subsystem 112 is connected to I/O bridge 107 or directly to CPU 102, rather than to memory bridge 105. In still other embodiments, I/O bridge 107 and memory bridge 105 might be integrated into a single chip. The particular components shown herein are optional; for instance, any number of add-in cards or peripheral devices might be supported. In some embodiments, switch 116 is eliminated, and network adapter 118 and add-in cards 120, 121 connect directly to I/O bridge 107.

Figure 2:
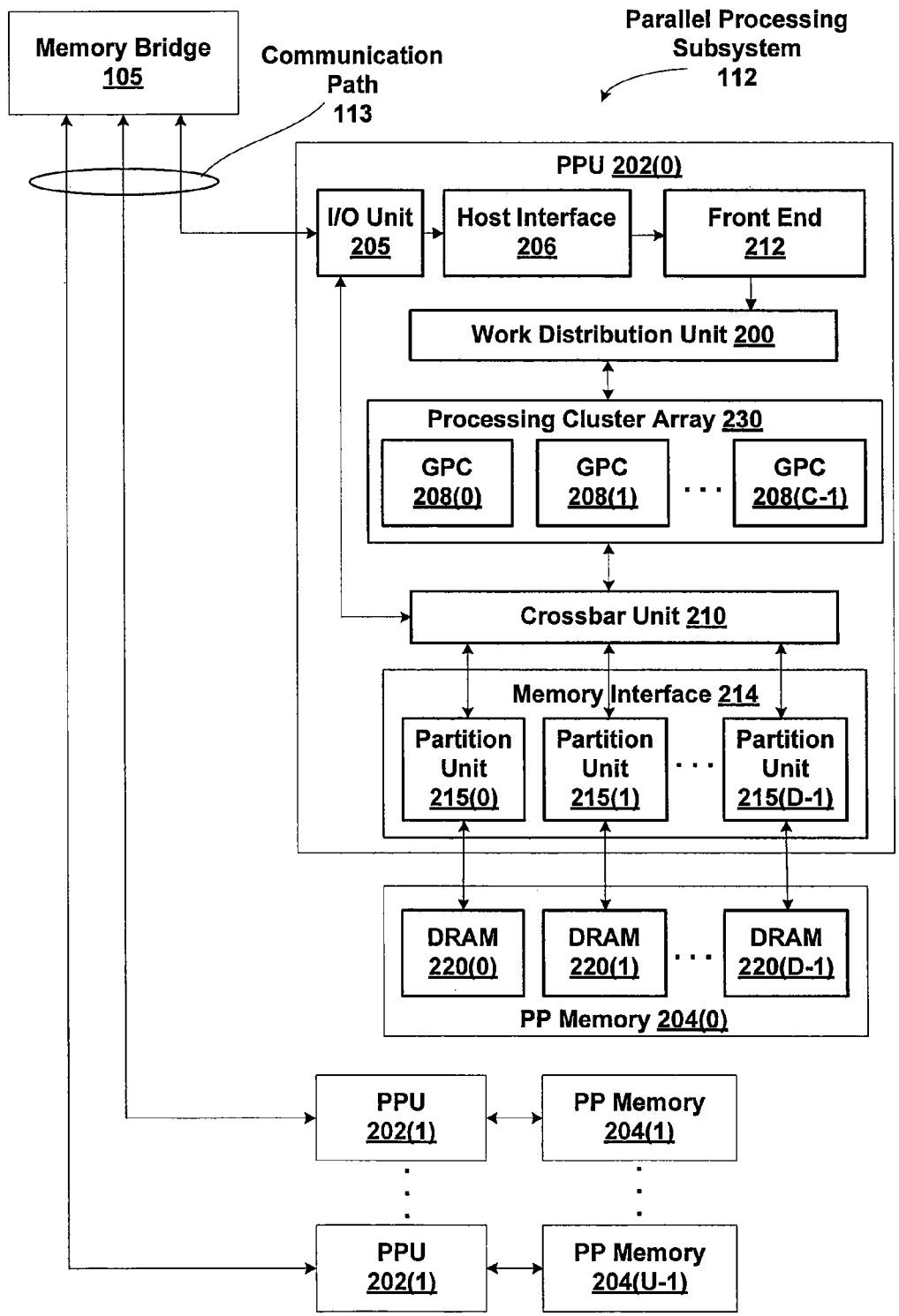
FIG. 2 is a block diagram of a parallel processing subsystem for the computer system of FIG. 1, according to one embodiment of the present invention.

FIG. 2 illustrates a parallel processing subsystem 112, according to one embodiment of the present invention. As shown, parallel processing subsystem 112 includes one or more parallel processing units (PPUs) 202, each of which is coupled to a local parallel processing (PP) memory 204. In general, a parallel processing subsystem includes a number U of PPUs, where $U \geq 1$. (Herein, multiple instances of like objects are denoted with reference numbers identifying the object and parenthetical numbers identifying the instance where needed.) PPUs 202 and parallel processing memories 204 may be implemented using one or more integrated circuit devices, such as programmable processors, application specific integrated circuits (ASICs), or memory devices, or in any other technically feasible fashion.

Referring again to FIG. 1, in some embodiments, some or all of PPUs 202 in parallel processing subsystem 112 are graphics processors with rendering pipelines that can be configured to perform various tasks related to generating pixel data from graphics data supplied by CPU 102 and/or system memory 104 via memory bridge 105 and bus 113, interacting with local parallel processing memory 204 (which can be used as graphics memory including, e.g., a conventional frame buffer) to store and update pixel data, delivering pixel data to display device 110, and the like. In some embodiments, parallel processing subsystem 112 may include one or more PPUs 202 that operate as graphics processors and one or more other PPUs 202 that are used for general-purpose computations. The PPUs may be identical or different, and each PPU may have its own dedicated parallel processing memory device(s) or no dedicated parallel processing memory device(s). One or more PPUs 202 may output data to display device 110 or each PPU 202 may output data to one or more display devices 110.

In operation, CPU 102 is the master processor of computer system 100, controlling and coordinating operations of other system components. In particular, CPU 102 issues commands that control the operation of PPUs 202. In some embodiments, CPU 102 writes a stream of commands for each PPU 202 to a pushbuffer (not explicitly shown in either FIG. 1 or FIG. 2) that may be located in system memory 104, parallel processing memory 204, or another storage location accessible to both CPU 102 and PPU 202. PPU 202 reads the command stream from the pushbuffer and then executes commands asynchronously relative to the operation of CPU 102.

Referring back now to FIG. 2, each PPU 202 includes an I/O (input/output) unit 205 that communicates with the rest of computer system 100 via communication path 113, which connects to memory bridge 105 (or, in one alternative embodiment, directly to CPU 102). The connection of PPU 202 to the rest of computer system 100 may also be varied. In some embodiments, parallel processing subsystem 112 is implemented as an add-in card that can be inserted into an expansion slot of computer system 100. In other embodiments, a PPU 202 can be integrated on a single chip with a bus bridge, such as memory bridge 105 or I/O bridge 107. In still other embodiments, some or all elements of PPU 202 may be integrated on a single chip with CPU 102.

In one embodiment, communication path 113 is a PCI-E link, in which dedicated lanes are allocated to each PPU 202, as is known in the art. Other communication paths may also be used. An I/O unit 205 generates packets (or other signals) for transmission on communication path 113 and also receives all incoming packets (or other signals) from communication path 113, directing the incoming packets to appropriate components of PPU 202. For example, commands related to processing tasks may be directed to a host interface 206, while commands related to memory operations (e.g., reading from or writing to parallel processing memory 204) may be directed to a memory crossbar unit 210. Host interface 206 reads each pushbuffer and outputs the work specified by the pushbuffer to a front end 212.

Each PPU 202 advantageously implements a highly parallel processing architecture. As shown in detail, PPU 202(0) includes a processing cluster array 230 that includes a number C of general processing clusters (GPCs) 208, where C≧1. Each GPC 208 is capable of executing a large number (e.g., hundreds or thousands) of threads concurrently, where each thread is an instance of a program. In various applications, different GPCs 208 may be allocated for processing different types of programs or for performing different types of computations. For example, in a graphics application, a first set of GPCs 208 may be allocated to perform tessellation operations and to produce primitive topologies for patches, and a second set of GPCs 208 may be allocated to perform tessellation shading to evaluate patch parameters for the primitive topologies and to determine vertex positions and other per-vertex attributes. The allocation of GPCs 208 may vary dependent on the workload arising for each type of program or computation.

GPCs 208 receive processing tasks to be executed via a work distribution unit 200, which receives commands defining processing tasks from front end unit 212. Processing tasks include indices of data to be processed, e.g., surface (patch) data, primitive data, vertex data, and/or pixel data, as well as state parameters and commands defining how the data is to be processed (e.g., what program is to be executed). Work distribution unit 200 may be configured to fetch the indices corresponding to the tasks, or work distribution unit 200 may receive the indices from front end 212. Front end 212 ensures that GPCs 208 are configured to a valid state before the processing specified by the pushbuffers is initiated.

A work distribution unit 200 may be configured to produce tasks at a frequency capable of providing tasks to multiple GPCs 208 for processing. By contrast, in conventional systems, processing is typically performed by a single processing engine, while the other processing engines remain idle, waiting for the single processing engine to complete its tasks before beginning their processing tasks. In some embodiments of the present invention, portions of GPCs 208 are configured to perform different types of processing. For example a first portion may be configured to perform vertex shading and topology generation, a second portion may be configured to perform tessellation and geometry shading, and a third portion may be configured to perform pixel shading in screen space to produce a rendered image. Intermediate data produced by GPCs 208 may be stored in buffers to allow the intermediate data to be transmitted between GPCs 208 for further processing.

Memory interface 214 includes a number D of partition units 215 that are each directly coupled to a portion of parallel processing memory 204, where D≧1. As shown, the number of partition units 215 generally equals the number of DRAM 220. In other embodiments, the number of partition units 215 may not equal the number of memory devices. Persons skilled in the art will appreciate that DRAM 220 may be replaced with other suitable storage devices and can be of generally conventional design. A detailed description is therefore omitted. Render targets, such as frame buffers or texture maps may be stored across DRAMs 220, allowing partition units 215 to write portions of each render target in parallel to efficiently use the available bandwidth of parallel processing memory 204.

Any one of GPCs 208 may process data to be written to any of the partition units 215 within parallel processing memory 204. Crossbar unit 210 is configured to route the output of each GPC 208 to the input of any partition unit 214 or to another GPC 208 for further processing. GPCs 208 communicate with memory interface 214 through crossbar unit 210 to read from or write to various external memory devices. In one embodiment, crossbar unit 210 has a connection to memory interface 214 to communicate with I/O unit 205, as well as a connection to local parallel processing memory 204, thereby enabling the processing cores within the different GPCs 208 to communicate with system memory 104 or other memory that is not local to PPU 202. Crossbar unit 210 may use virtual channels to separate traffic streams between the GPCs 208 and partition units 215.

Again, GPCs 208 can be programmed to execute processing tasks relating to a wide variety of applications, including but not limited to, linear and nonlinear data transforms, filtering of video and/or audio data, modeling operations (e.g., applying laws of physics to determine position, velocity and other attributes of objects), image rendering operations (e.g., tessellation shader, vertex shader, geometry shader, and/or pixel shader programs), and so on. PPUs 202 may transfer data from system memory 104 and/or local parallel processing memories 204 into internal (on-chip) memory, process the data, and write result data back to system memory 104 and/or local parallel processing memories 204, where such data can be accessed by other system components, including CPU 102 or another parallel processing subsystem 112.

A PPU 202 may be provided with any amount of local parallel processing memory 204, including no local memory, and may use local memory and system memory in any combination. For instance, a PPU 202 can be a graphics processor in a unified memory architecture (UMA) embodiment. In such embodiments, little or no dedicated graphics (parallel processing) memory would be provided, and PPU 202 would use system memory exclusively or almost exclusively. In UMA embodiments, a PPU 202 may be integrated into a bridge chip or processor chip or provided as a discrete chip with a high-speed link (e.g., PCI-E) connecting the PPU 202 to system memory via a bridge chip or other communication means.

As noted above, any number of PPUs 202 can be included in a parallel processing subsystem 112. For instance, multiple PPUs 202 can be provided on a single add-in card, or multiple add-in cards can be connected to communication path 113, or one or more of PPUs 202 can be integrated into a bridge chip. PPUs 202 in a multi-PPU system may be identical to or different from one another. For instance, different PPUs 202 might have different numbers of processing cores, different amounts of local parallel processing memory, and so on. Where multiple PPUs 202 are present, those PPUs may be operated in parallel to process data at a higher throughput than is possible with a single PPU 202. Systems incorporating one or more PPUs 202 may be implemented in a variety of configurations and form factors, including desktop, laptop, or handheld personal computers, servers, workstations, game consoles, embedded systems, and the like.

Processing Cluster Array Overview

Figure 3A:
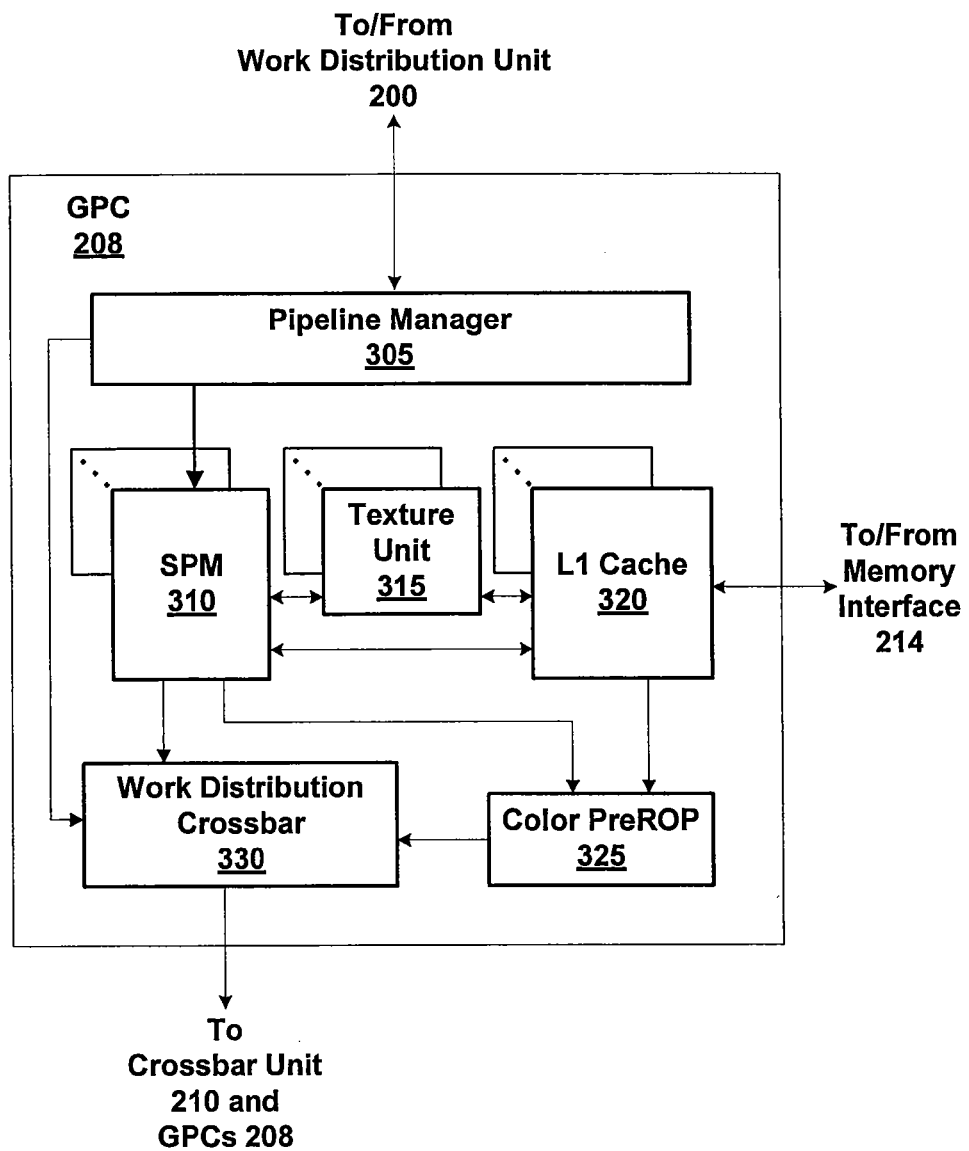
FIG. 3A is a block diagram of a GPC within one of the PPUs of FIG. 2, according to one embodiment of the present invention.

FIG. 3A is a block diagram of a GPC 208 within one of the PPUs 202 of FIG. 2, according to one embodiment of the present invention. Each GPC 208 may be configured to execute a large number of threads in parallel, where the term "thread" refers to an instance of a particular program executing on a particular set of input data. In other embodiments, single-instruction, multiple-data (SIMD) instruction issue techniques are used to support parallel execution of a large number of threads without providing multiple independent instruction units. In other embodiments, single-instruction, multiple-thread (SIMT) techniques are used to support parallel execution of a large number of generally synchronized threads, using a common instruction unit configured to issue instructions to a set of processing engines within each one of the GPCs 208. Unlike a SIMD execution regime, where all processing engines typically execute identical instructions, SIMT execution allows different threads to more readily follow divergent execution paths through a given thread program. Persons skilled in the art will understand that a SIMD processing regime represents a functional subset of a SIMT processing regime.

In graphics applications, a GPU 208 may be configured to implement a primitive engine 304 for performing screen space graphics processing functions that may include, but are not limited to primitive setup, rasterization, and z culling. In some embodiments, primitive engine 304 is configured to gather pixels into tiles of multiple neighboring pixels before outputting the pixels to L1 cache 320 in order to improve the access efficiency of L1 cache 320. Primitive engine 304 receives a processing task from work distribution unit 200, and when the processing task does not require the operations performed by primitive engine 304, the processing task is passed through primitive engine 304 to a pipeline manager 305. Operation of GPC 208 is advantageously controlled via a pipeline manager 305 that distributes processing tasks to streaming multiprocessors (SPMs) 310. Pipeline manager 305 may also be configured to control a work distribution crossbar 330 by specifying destinations for processed data output by SPMs 310.

In one embodiment, each GPC 208 includes a number M of SPMs 310, where M≧1, each SPM 310 configured to process one or more thread groups. Also, each SPM 310 advantageously includes an identical set of functional units (e.g., arithmetic logic units, etc.) that may be pipelined, allowing a new instruction to be issued before a previous instruction has finished, as is known in the art. Any combination of functional units may be provided. In one embodiment, the functional units support a variety of operations including integer and floating point arithmetic (e.g., addition and multiplication), comparison operations, Boolean operations (AND, OR, XOR), bit-shifting, and computation of various algebraic functions (e.g., planar interpolation, trigonometric, exponential, and logarithmic functions, etc.); and the same functional-unit hardware can be leveraged to perform different operations.

The series of instructions transmitted to a particular GPC 208 constitutes a thread, as previously defined herein, and the collection of a certain number of concurrently executing threads across the parallel processing engines (not shown) within an SPM 310 is referred to herein as a "warp" or "thread group." As used herein, a "thread group" refers to a group of threads concurrently executing the same program on different input data, with one thread of the group being assigned to a different processing engine within an SPM 310. A thread group may include fewer threads than the number of processing engines within the SPM 310, in which case some processing engines will be idle during cycles when that thread group is being processed. A thread group may also include more threads than the number of processing engines within the SPM 310, in which case processing will take place over consecutive clock cycles. Since each SPM 310 can support up to G thread groups concurrently, it follows that up to GXM thread groups can be executing in GPC 208 at any given time.

Additionally, a plurality of related thread groups may be active (in different phases of execution) at the same time within an SPM 310. This collection of thread groups is referred to herein as a "cooperative thread array" ("CIA"). The size of a particular CTA is equal to m*k, where k is the number of concurrently executing threads in a thread group and is typically an integer multiple of the number of parallel processing engines within the SPM 310, and m is the number of thread groups simultaneously active within the SPM 310. The size of a CTA is generally determined by the programmer and the amount of hardware resources, such as memory or registers, available to the CTA.

Each SPM 310 uses space in a corresponding L1 cache 320 that is used to perform load and store operations. Each SPM 310 also has access to L2 caches within the partition units 215 that are shared among all GPCs 208 and may be used to transfer data between threads. Finally, SPMs 310 also have access to off-chip "global" memory, which can include, e.g., parallel processing memory 204 and/or system memory 104. It is to be understood that any memory external to PPU 202 may be used as global memory.

In graphics applications, a GPC 208 may be configured such that each SPM 310 is coupled to a texture unit 315 for performing texture mapping operations, e.g., determining texture sample positions, reading texture data, and filtering the texture data. Texture data is read from L1 cache 320 and is fetched from an L2 cache, parallel processing memory 204, or system memory 104, as needed. Each SPM 310 outputs processed tasks to work distribution crossbar 330 in order to provide the processed task to another GPC 208 for further processing or to store the processed task in an L2 cache, parallel processing memory 204, or system memory 104 via crossbar unit 210. A color preROP (pre-raster operations) 325 is configured to perform optimizations for color blending, organize pixel color data, and perform address translations.

It will be appreciated that the core architecture described herein is illustrative and that variations and modifications are possible. Any number of processing engines, e.g., primitive engines 304, SPMs 310, texture units 315, or color preROPs 325 may be included within a GPC 208. Further, while only one GPC 208 is shown, a PPU 202 may include any number of GPCs 208 that are advantageously functionally similar to one another so that execution behavior does not depend on which GPC 208 receives a particular processing task. Further, each GPC 208 advantageously operates independently of other GPCs 208 using separate and distinct processing engines, L1 caches 320, and so on.

Figure 3B:
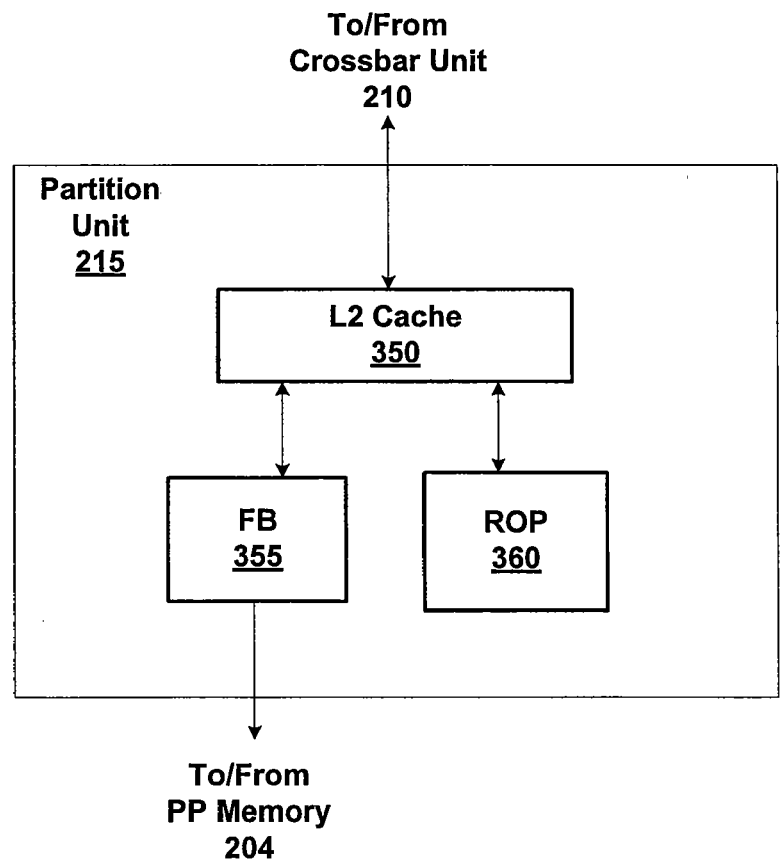
FIG. 3B is a block diagram of a partition unit within one of the PPUs of FIG. 2, according to one embodiment of the present invention.

FIG. 3B is a block diagram of a partition unit 215 within on of the PPUs 202 of FIG. 2, according to one embodiment of the present invention. As shown, partition unit 215 includes a L2 cache 350, a frame buffer (FB) 355, and a raster operations unit (ROP) 360. L2 cache 350 is a read/write cache that is configured to perform load and store operations received from crossbar unit 210 and ROP 360. In some embodiments, L2 cache 350 may be split into four (or fewer) slices in order to interface with memory crossbar unit 210 at four times the bandwidth of FB 355. Read misses and urgent writeback requests are output by L2 cache 350 to FB 355 for processing. Dirty updates are also sent to FB 355 for opportunistic processing. FB 355 interfaces directly with parallel processing memory 204, outputting read and write requests and receiving data read from parallel processing memory 204.

In graphics applications, ROP 360 is a processing unit that performs raster operations, such as stencil, z test, and the like, and outputs pixel data as processed graphics data for storage in graphics memory. The processed graphics data may be displayed on display device 110 or routed for further processing by CPU 102 or by one of the processing entities within parallel processing subsystem 112. Each partition unit 215 includes a ROP 360 in order to distribute processing of the raster operations. In some embodiments, ROP 360 is configured to compress z or color data that is written to memory and decompress z or color data that is read from memory.

Figure 3C:
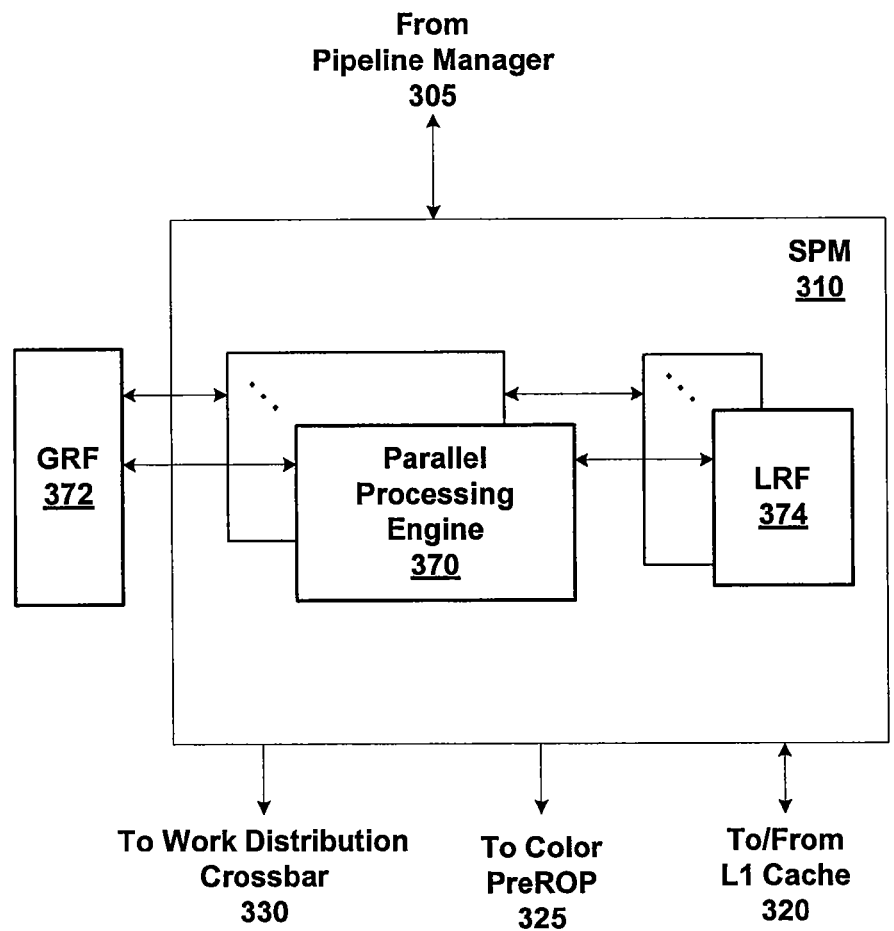
FIG. 3C is a conceptual diagram of a streaming multiprocessor (SPM) within a general processing cluster of FIG. 2, according to one embodiment of the present invention.

FIG. 3C is a conceptual diagram of a streaming multiprocessor (SPM) 310 within a general processing cluster 208 of FIG. 2, according to one embodiment of the present invention. The SPM 310 includes at least one parallel processing engine 370, at least one global register file (GRF) 372 and at least one local register file (LRF) 374 per parallel processing engine 370. As previously described herein, each parallel processing engine 370 may be configured to execute one or more instances of a given program as individual threads, wherein each thread may operate on different data than other threads in a given execution cycle. In one embodiment the LRF 374 provides data storage that is local to each parallel processing engine 370 and may be associated with a specific thread, and the GRF 372 provides data storage accessible to each parallel processing engine 370.

The GRF 372 may be configured to provide simultaneous access to multiple different registers within the GRF 372 by multiple threads executing on one or more parallel processing engines 370. In one embodiment, simultaneous access to a plurality of registers, each associated with one of a plurality of memory alignments, may be performed in a given execution cycle. The GRF 372 may be configured to be accessed by more than one SPM 310.

Persons skilled in the art will understand that the architecture described in FIGS. 1, 2, 3A, 3B and 3C in no way limits the scope of the present invention and that the techniques taught herein may be implemented on any properly configured processing unit, including, without limitation, one or more CPUs, one or more multi-core CPUs, one or more PPUs 202, one or more GPCs 208, one or more graphics or special purpose processing units, or the like, without departing the scope of the present invention.

Efficient N-Body Computation Technique

Figure 4A:
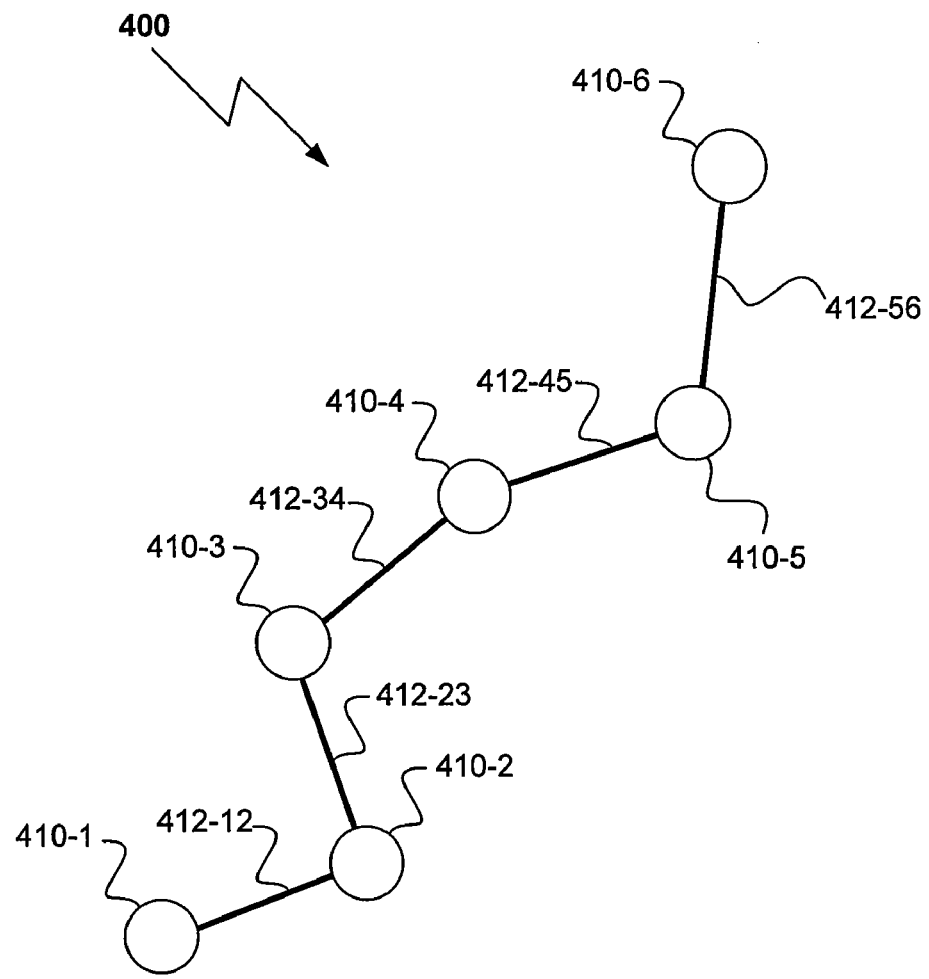
FIG. 4A represents a molecule comprising a plurality of atoms.

FIG. 4A represents a molecule 400 comprising a plurality of atoms 410. Each atom 410 is bound to at least one other atom 410 via a bond 412. For example atom 410-1 is bound to atom 410-2 via bond 412-12, and atom 410-2 is further bound to atom 410-3 via bond 412-23.

Figure 4B:
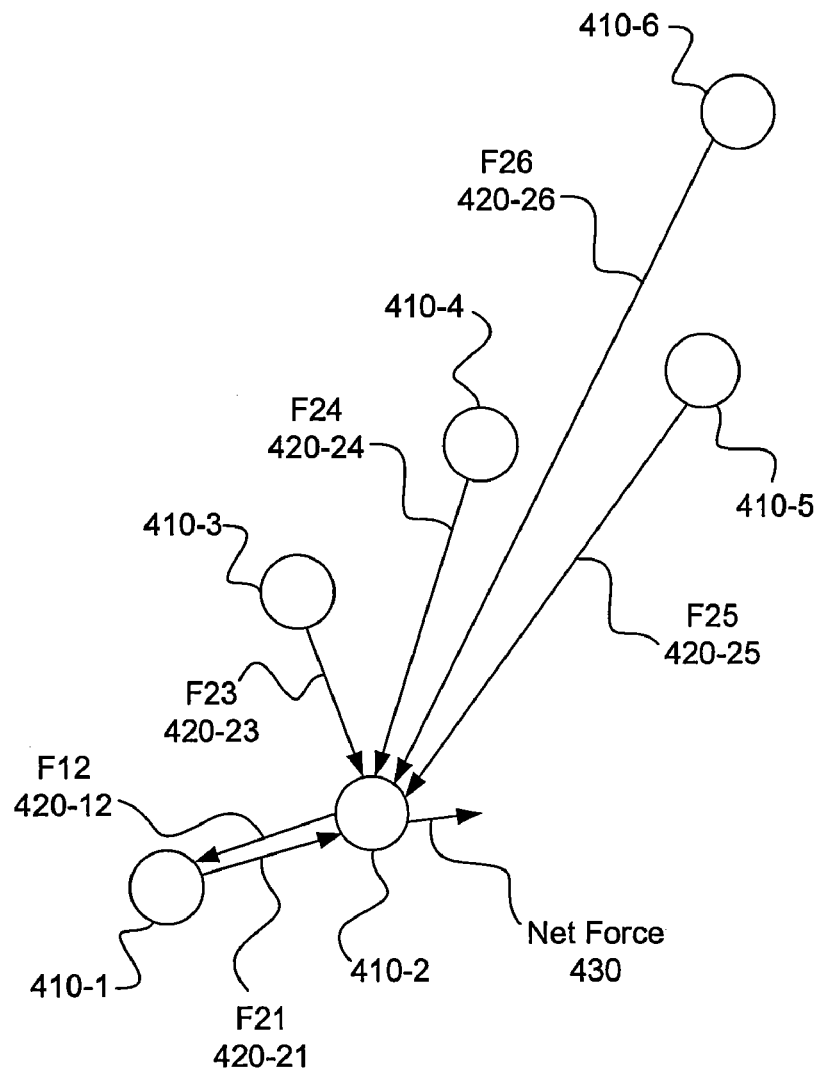
FIG. 4B illustrates forces between one atom within the molecule and other atoms within the molecule.

FIG. 4B illustrates forces 420 between one atom 410-2 within the molecule 400 and other atoms 410 within the molecule 400. The superposition of inter-atomic forces F21 420-21 through F 26 420-26 on atom 410-2 comprises a net force 430. Each force 420 may be calculated using any technically feasible technique.

Two inter-atomic forces may be represented between any two given atoms, and, importantly, the two inter-atomic forces are equal and opposite with respect to each atom. For example, with respect to atom 410-2, inter-atomic force F21 420-21 represents a force imparted on atom 410-2 by atom 410-1. However, with respect to atom 410-1, inter-atomic force F12 420-12 represented a force imparted on atom 410-1 by atom 410-2. In this scenario, force F21 420-21 is equal and opposite to force F12 420-12. In an optimal setting, a force between two atoms should only be computed fully once for computing a net force on the first of two atoms, and inverted for computing a net force on the second of two atoms.

Figure 5A:
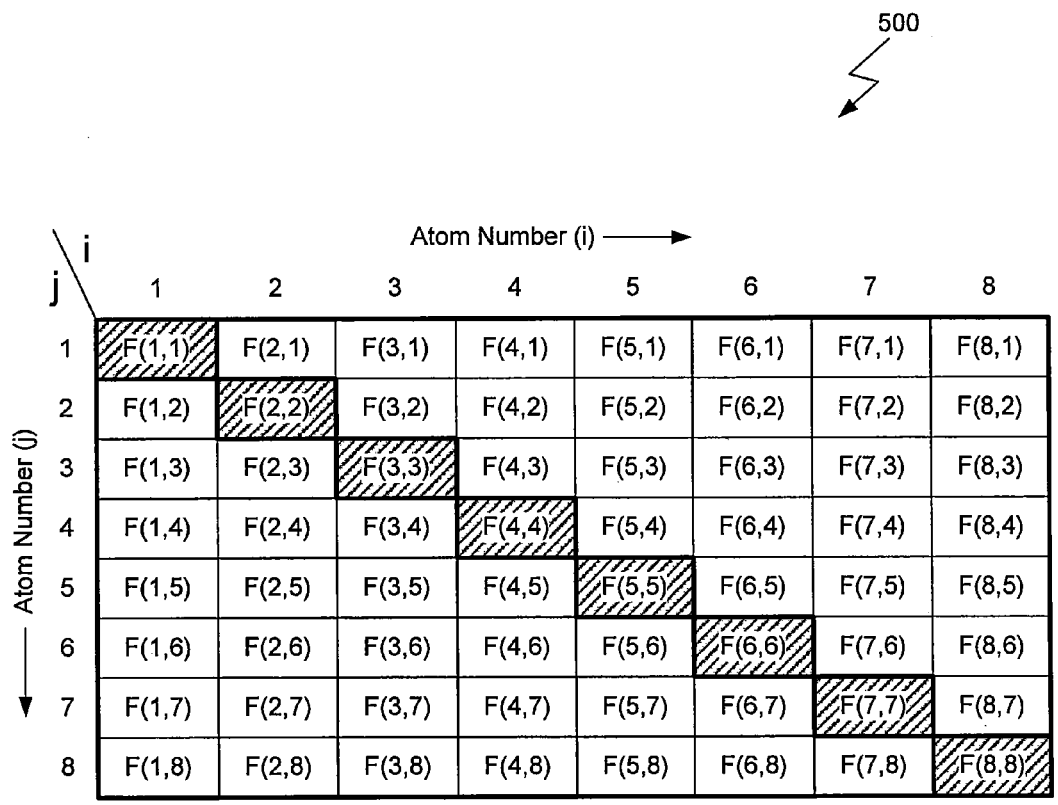
FIG. 5A illustrates a force matrix used to represent inter-atomic forces between individual atoms within a molecule, according to one embodiment of the present invention.

FIG. 5A illustrates a force matrix 500 used to represent inter-atomic forces between individual atoms within a molecule, according to one embodiment of the present invention. The force matrix 500 includes two indices "i" and "j" that each index to an atom from an enumerated list of atoms. The enumerated list of atoms may include atoms comprising a complete molecule, such as a complete protein. Each cell F(i,j) within the force matrix 500 may be used to store a force between two atoms from the enumerated list of atoms selected by the two indices "i" and "j." For example, cell F(4,2) of force matrix 500 stores a force between atom 4 from the enumerated list of atoms and atom 2 from the enumerated list of atoms. Similarly, cell F(2,4) may store a matching inverse force between atom 2 from the enumerated list of atoms and atom 4 from the enumerated list of atoms. The matching inverse force represented in F(2,4) should be equal and opposite to the force represented in F(4,2). In general, each force F(i,j) within the force matrix 500 includes a matching inverse force represented as F(j,i). Diagonal cells (F(i,j), for i=j) in the force matrix 500 comprise a special case where both indices refer to the same atom. Diagonal cells, shown highlighted with a hash pattern, need not include a force value.

Figure 5B:
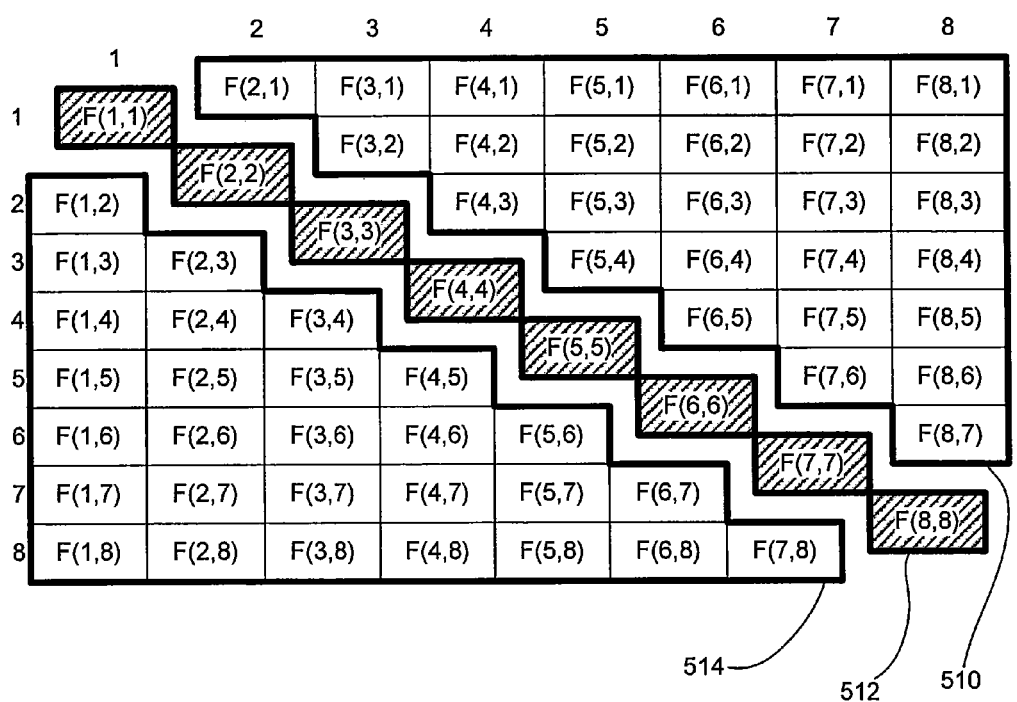
FIG. 5B illustrates an upper set, lower set, and diagonal set of cells within the force matrix, according to one embodiment of the present invention.

FIG. 5B illustrates an upper set 510, lower set 514, and diagonal set 512 of cells within the force matrix 500, according to one embodiment of the present invention. In one embodiment, only cells within the upper set 510 are computed and stored within the force matrix 500. Cells in the diagonal set 512 should contribute a zero net force to each respective atom and are not needed for force computations on a given atom. Furthermore, each cell F(i,j) within the lower set 514 that represents a respective force between two indicated atoms has a matching inverse force as cell F(j,1) within the upper set 510.

FIG. 5C is an exemplary partitioning of the force matrix 500 for assignment to thread groups within one or more PPUs 202 of FIG. 2, according to one embodiment of the present invention. The force matrix 500 is partitioned into tiles 520, 522, 524, 526 for processing by at least one SPM 310 within the one or more PPUs 202. On-diagonal tiles 524, 526 include cells from the diagonal set 512, while off-diagonal tiles 520, 522 do not include cells from the diagonal set 512. In one embodiment, each tile 520, 522, 524, 526 is assigned to a thread group for processing. Importantly, because each thread group only acts on data within an assigned tile, each thread group may process the assigned tile to completion without regard to other thread groups or synchronization with the other thread groups. After all thread groups processing a given force matrix 500 have completed, computation may proceed with no additional synchronization among the thread groups. Greater overall efficiency may be achieved by relieving the threads from requiring intermediate synchronization.

Figure 6A:
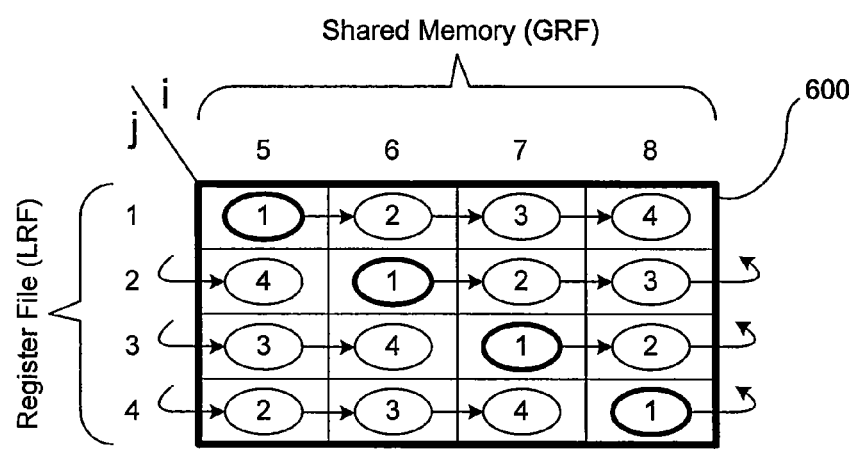
FIG. 6A illustrates processing an off-diagonal tile within the force matrix, according to one embodiment of the present invention.

FIG. 6A illustrates processing an off-diagonal tile 600 within the force matrix 500, according to one embodiment of the present invention. The off-diagonal tile 600, such as off-diagonal tile 520, includes a rectangular sub-matrix of the force matrix 500. In one embodiment, the off-diagonal tile 600 is sized according to a number of threads the SPM 310 is able to process simultaneously in a "warp" or "thread group." For example, if the SPM 310 is able to process four threads simultaneously as a thread group, then the off-diagonal tile 600 may be sized as a 4×4 sub-matrix of force matrix 500. Each unique "j" index within the off-diagonal tile 600 should be assigned to a thread for processing. Each thread traverses horizontally within the off-diagonal tile 600 by performing a set of iterations bounded by a width for the off-diagonal tile 600. At each iteration, the thread increments the "i" index to refer to a subsequent cell within the off-diagonal tile 600. The increment function should wrap the value of the "i" index about the horizontal boundaries of the off-diagonal tile 600.

Each thread combines a respective "i" value with an assigned "j" value for the thread into a tile cell index comprising the "i,j" values. The tile cell index is used to call a force computation function that returns a force value corresponding to a force between two atoms indicated by the two values within the tile cell index. The force value is stored in a respective cell within the off-diagonal tile 600. In one embodiment, the force value comprises three orthogonal force components, including a force component along an x-axis (Fx), a force component along a y-axis (Fy), and a force component along a z-axis (Fz).

In one embodiment, the off-diagonal tile 600 may be assigned to four threads (numbered 1 to 4) within a thread group, corresponding to j=1 through j=4. Each of the four threads calls the force computation function once for each of four combinations represented in an assigned row. Each thread may read and write data from a local register file, such as LRF 374 of FIG. 3C. For example, data related to atom "j" may be loaded into storage within the LRF 374 associated with thread "j" and used by the force computation function.

Each thread may also read and write data from shared memory, such as GRF 372. For example, in a first iteration, thread 1 may load data for atom 1 into registers within LRF 374 and access data for atom 5 within the GRF 372. Each access may comprise a read, a write, or a combination of reads and writes to a specific location within the GRF 372. Importantly, each thread is able to access each location within the GRF 372. As a given thread iterates through cells comprising a width of the off-diagonal tile 600, the thread accesses contiguously adjacent data within the GRF 372. Each thread within the thread group accesses each associated item of data in the GRF 372 once the off-diagonal tile has been processed.

Because each thread within the thread group is executing instructions that are synchronized with other threads within the thread group, multiple simultaneous accesses to memory will likely occur whenever any access to memory occurs. To mitigate access conflicts that may result from multiple simultaneous accesses to the GRF 372, each thread staggers access over a set of address offsets. Each address offset is structured to avoid access conflicts. Each offset is incremented per iteration, causing each thread to access data for an adjacent atom along a contiguous horizontal span of atoms associated with the off-diagonal tile 600.

Each of four iterations needed to process the 4×4 tile are labeled by an oval associated with each cell within the off-diagonal tile 600. During the first iteration (labeled as "1" within each oval), thread 1 accesses data within the GRF 372 related to atom 5 to process a force between atom 1 and atom 5, and thread 2 accesses data related to atom 6 to process a force between atom 2 and atom 6, and so forth. During a second iteration (labeled as "2" within each oval), thread 2 accesses data for atom 7. During a third iteration (labeled as "3" within each oval), thread 2 accesses data for atom 8. During a fourth iteration (labeled as "4" within each oval), thread 2 accesses data for atom 5, and thread 1 accesses data for atom 8. By staggering access to data within the GRF 372, access conflicts may be avoided.

In on embodiment the SPM 310 is able to process thirty-two threads simultaneously as a thread group and the off-diagonal tile 600 comprises thirty-two by thirty-two cells, wherein each row of thirty-two cells is assigned to one of thirty-two threads within the thread group. Persons skilled in the art will recognize that each thread group within a collection of thread groups is able to process a respective off-diagonal tile to completion without interacting or synchronizing with other thread blocks, and that different tile sizes may be implemented without departing from the scope of the invention.

Figure 6B:
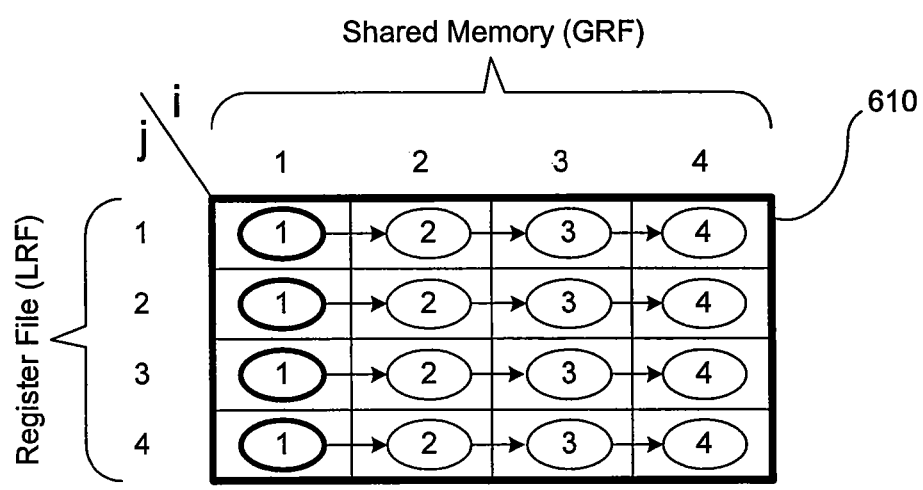
FIG. 6B illustrates processing an on-diagonal tile within the force matrix, according to one embodiment of the present invention.

FIG. 6B illustrates processing an on-diagonal tile 610 within the force matrix 500, according to one embodiment of the present invention. In a first iteration, thread 1 processes an inter-atom force from atom 1 to atom 1, thread 2 processes an inter-atom force atom 2 to atom 1, and so on. Persons skilled in the art will recognize that the technique described in FIG. 6A may also be applied to on-diagonal tiles.

Figure 7:
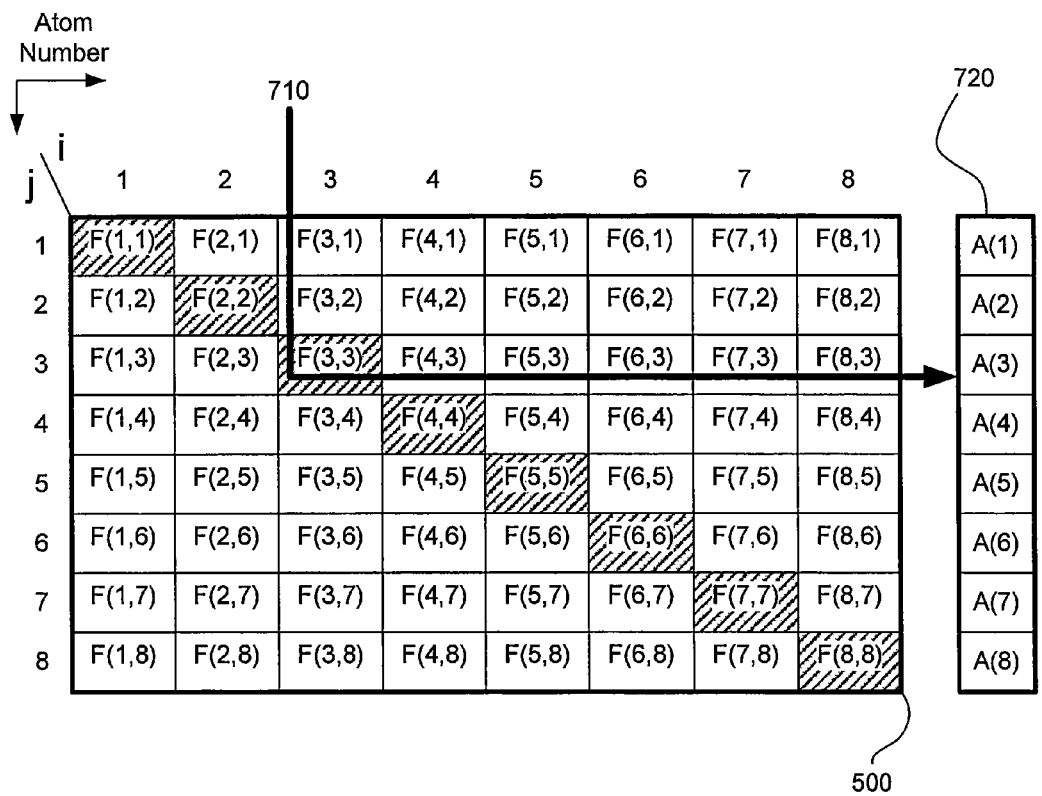
FIG. 7 illustrates a technique for computing a net force for an atom from individual inter-atomic forces within the force matrix, according to one embodiment of the invention.

FIG. 7 illustrates a technique for computing a net force for an atom from individual inter-atomic forces within the force matrix 500, according to one embodiment of the invention. To compute a net force for a given atom, forces from surrounding atoms acting on the atom should be added together. In the context of force matrix 500, each force between the given atom and each other atom is added together using a reduction operation and stored in an output buffer 720, which includes storage for each atom in the enumerated list of atoms. For example, to compute a net force for atom 8, each force relative to atom 8 should be added together, specifically, F(8,1), F(8, 2), F(8,3), and so forth, ending with F(8,8). A resulting sum is stored in output buffer 720 at location A(8). In general, a traversal path 710 can be used to specify a set of cells within force matrix 500 should be added together to produce a sum comprising a net force on a given atom number.

In one embodiment, the traversal path starts at j=1 and i=atom_number to sum. The traversal path 710 proceeds along increasing "j" values (vertically downward) until reaching a corresponding diagonal cell, at which point "j" remains constant and the traversal path 710 proceeds along increasing "i" values until the horizontal boundary of the force matrix 500 is reached. Each cell within the force matrix 500 intersected by the traversal path 710 contributes to a final sum, stored in the output buffer 720. Cells intersected along the vertical portion of the traversal path 710 are added to the final sum, while cells intersected along the horizontal portion of the traversal path 710 are inverted before being added to the final sum, which corresponds to a net force on the given atom.

For example, to compute net forces on atom 3, the traversal path 710 specifies cells F(3,1), F(3,2), F(3,3), which are relative to atom 3. The traversal path 710 then specifies cells that store matching inverse forces relative to atom 3, specifically F(4,3), F(5,3), F(6,3), F(7,3), and F(8,3). The matching inverse forces are first inverted and then added to final sum for atom 3 to produce a correct sum, which is stored in entry A(3) of output buffer 720.

Each final sum may comprise a three-dimensional force vector, wherein each three-dimensional force vector includes three orthogonal component forces. In one embodiment, each component force is computed by a thread. That is, three threads are used to compute the three-dimensional force vector.

Persons skilled in the art will recognize that data within the force matrix 500 should be organized for efficient coalescing of simultaneous access requests generated by a plurality of threads. Similarly, data within the output buffer 720 should be organized to facilitate efficient simultaneous access by the plurality of threads.

In one embodiment, for scenarios with a large number of atoms (N) with respect to available processing threads (P), that is N>>P, each processing thread may accumulate a final sum value locally rather than write the final sum value to the output buffer 720. In this way, access conflicts to output buffer 720 may be mitigated.

Persons skilled in the art will recognize that certain forces between atoms having specific relationships should be excluded for the purpose of molecular dynamic modeling. For example, atoms having certain bond, bond angle, or dihedral relationships should be excluded from the computations described previously. Each tile within the force matrix 500 references a set of atoms along the vertical axis and a set of atoms along the horizontal axis. To represent exclusion relationships between atoms within the tile, an exclusion flag may be set for each cell (an intersection of two atoms) within the tile.

In one embodiment implementing a 32×32 tile, a data structure including a 32-bit word for each atom within the tile is allocated to represent exclusion relationships between a given atom along the vertical axis and atoms along the horizontal axis. Each bit of the 32-bit word may be set to indicate that a corresponding atom should be excluded or included in inter-atom force calculations.

Figure 8:
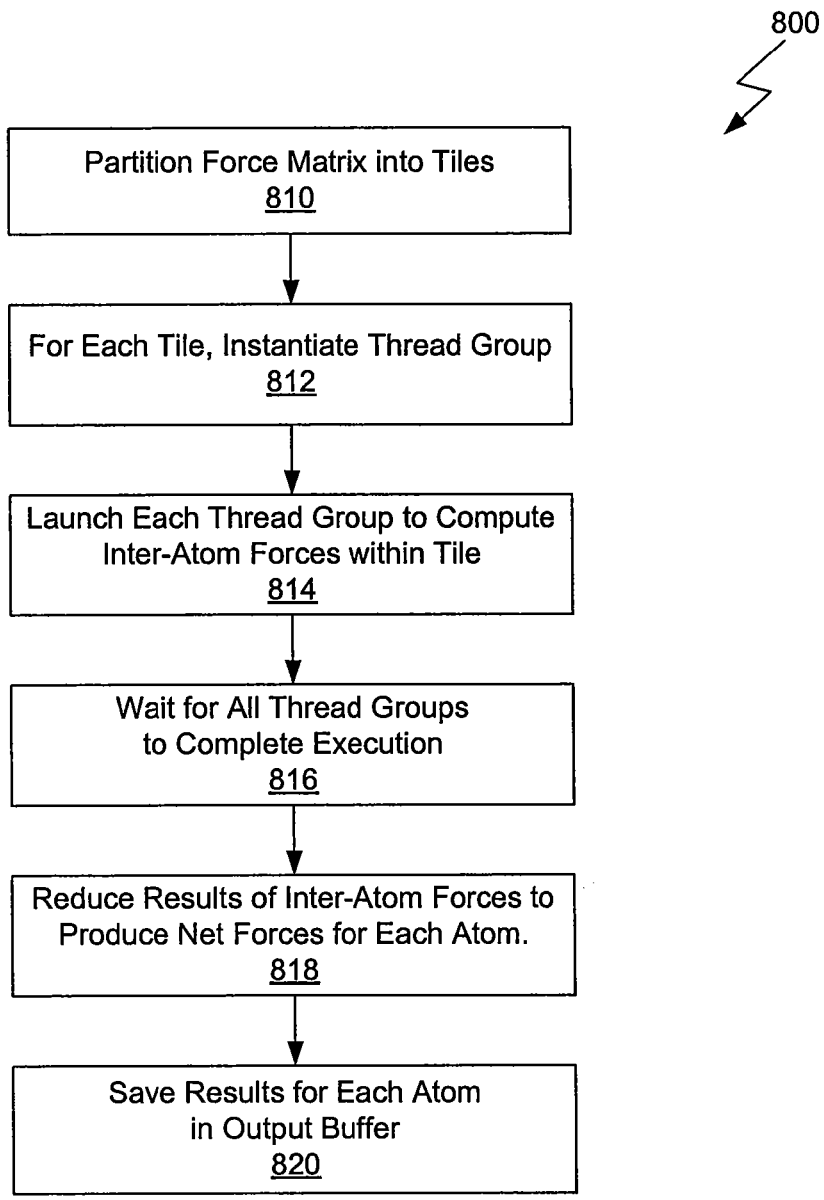
FIG. 8 is a flow diagram of method steps for computing net forces on atoms in an N-body system, according to one embodiment of the invention.

FIG. 8 is a flow diagram of method steps 800 for computing net forces on atoms in an N-body system, according to one embodiment of the invention. Although the method steps are described in conjunction with the systems of FIGS. 1, 2, and 3A to 3C, persons skilled in the art will understand that any system that performs the method steps, in any order, is within the scope of the invention. The method computes net forces, which may be used in molecular dynamic modeling systems, such as protein folding simulation systems.

The method begins in step 810, where a PPU partitions an allocated force matrix into a set of tiles. The force matrix should include N×N cells, where N is a number of atoms in an N-body system. In one embodiment, each tile includes T×T cells, where T is a number of threads that may operate together as a thread group. In step 812, for each tile, the PPU instantiates a thread group per tile within the force matrix. In step 814, the PPU launches the thread groups to compute inter-atom forces within the tile, as described in FIGS. 5A-6B. Results of the inter-atom force computations are stored in the force matrix. Once launched, each thread group operating on a given tile may perform computations independently of each other thread group. In step 816, the PPU waits for all thread groups launched in step 814 to complete execution. In step 818, the PPU instantiates and launches at least one set of thread groups to perform a reduction operation, as described in FIGS. 7 and 10, on inter-atom forces stored in the force matrix to produce net forces for each atom. In step 820, the PPU saves results for each atom in at least one output buffer. In one embodiment, the at least one output buffer is stored within a GRF. In an alternative embodiment, the at least one output buffer is stored in an LRF.

Figure 9:
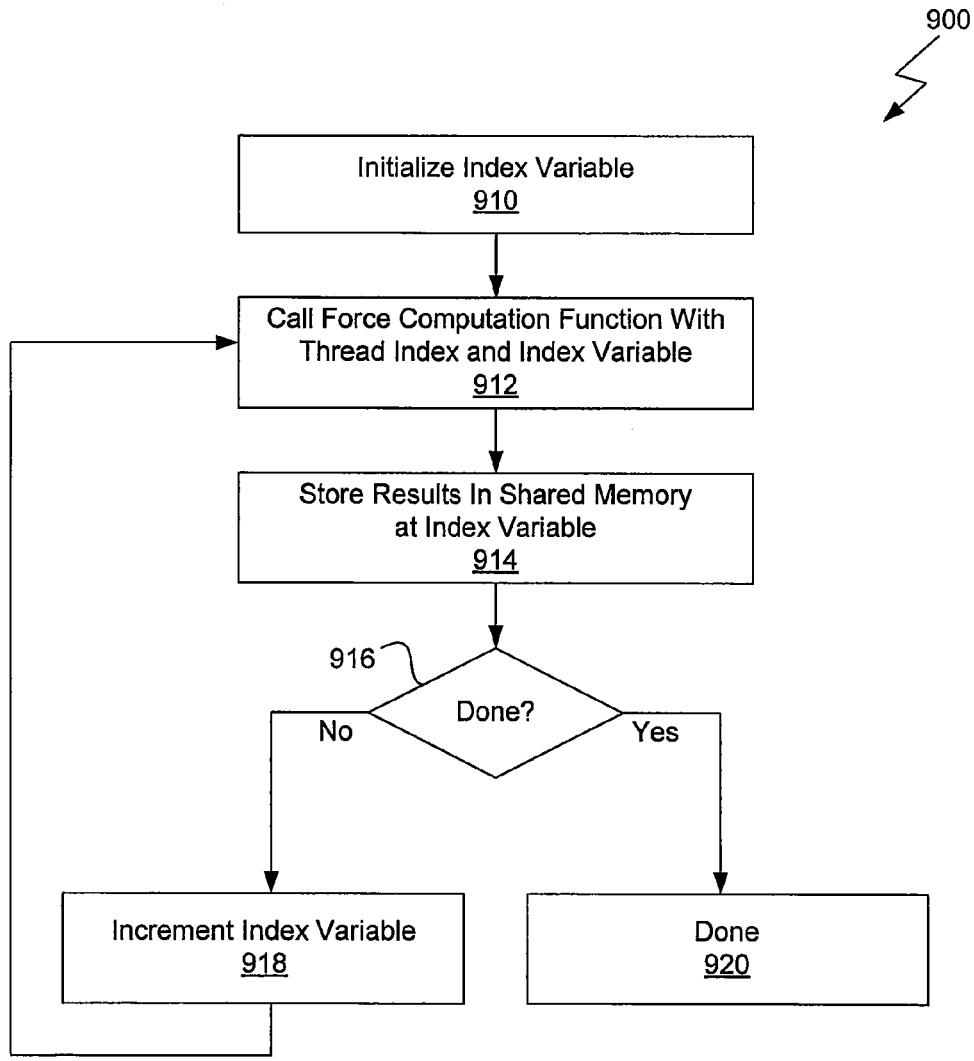
FIG. 9 is a flow diagram of method steps for computing inter-atomic forces represented by a tile, according to one embodiment of the invention.

FIG. 9 is a flow diagram of method steps for computing inter-atomic forces represented by a tile, according to one embodiment of the invention. Although the method steps are described in conjunction with the systems of FIGS. 1, 2, and 3A to 3C, persons skilled in the art will understand that any system that performs the method steps, in any order, is within the scope of the invention. This method is performed by a thread within a thread group operating on a tile stored in the force matrix. The thread group may execute within a PPU. In one embodiment, this method is used in performing step 814 of FIG. 8.

The method begins in step 910, where the thread within the thread group initializes an index variable. In one embodiment the index variable is initialized according to a thread identification number (thread ID). In one embodiment, a first thread in a thread group is identified as thread ID zero, while a first horizontal cell may be identified as having an index of one. In this scenario, the index variable is initialized to a thread ID value plus one. Persons skilled in the art will recognize that a thread ID as well as an array index may commonly start at zero or one. However, in generic terms, a first thread initializes the index variable to a first horizontal position within the tile; a second thread initializes the index variable to a second horizontal position within the tile, and so forth. In an alternative embodiment, each thread within the thread group initializes the index variable to point to a first horizontal cell within the tile.

In step 912, the thread calls a force computation function with a thread index derived from a thread identification number, and the index variable. Any technically feasible technique may be used by the force computation function to compute an inter-atom force. In step 914, the thread stores the inter-atom force results in a shared memory at a location determined by the index variable.

If, in step 916 the index variable has not iterated through each horizontal location within the tile, then the thread is not done and the method proceeds to step 918. In one embodiment, the thread tests if the index variable has iterated through each horizontal location by testing total iteration count against the tile width. In this scenario, the thread should perform a number of iterations equal to the horizontal width minus one. In step 918, the thread increments the index variable. If the index variable points to the rightmost location within the tile, then the increment operation wraps the index variable back to the leftmost location within the tile. The method then proceeds to step 912.

Returning to step 916, if the index variable has iterated through each horizontal location within the tile, then the thread is done and the method terminates in step 920.

Figure 10:
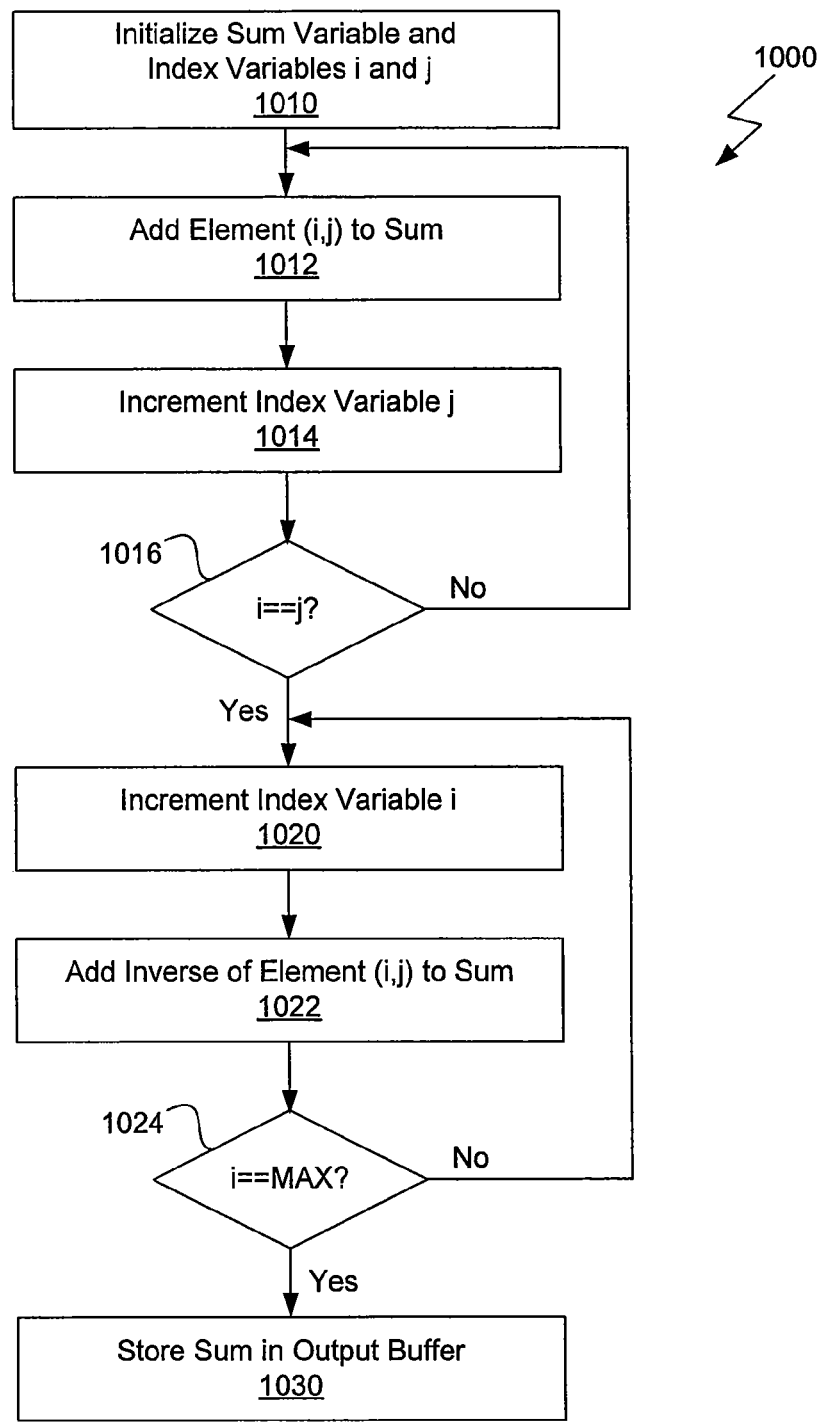
FIG. 10 is a flow diagram of method steps for reducing inter-atomic forces within the force matrix to generate net forces on each atom, according to one embodiment of the invention.

FIG. 10 is a flow diagram of method steps for reducing inter-atomic forces within the force matrix to generate net forces on each atom, according to one embodiment of the invention. Although the method steps are described in conjunction with the systems of FIGS. 1, 2, and 3A to 3C, persons skilled in the art will understand that any system that performs the method steps, in any order, is within the scope of the invention. In one embodiment, this method is performed by a thread within a thread group to compute a reduction operation in step 818 of FIG. 8 for one atom.

In one embodiment, the sum variable includes one force component corresponding to one of three force components associated with an inter-atomic force. Three threads are used to independently compute each of the three force components to generate three sum components stored in an output buffer. The three threads may execute in three different thread groups or, alternatively, within the same thread group. In an alternative embodiment, the sum variable includes three components, and only one thread is used to compute three sum components stored in the output buffer.

The method begins in step 1010, where the thread initializes a sum variable, index variable i, and index variable j. In step 1012, the thread adds contents of cell (i,j) of the tile (referred to herein as F(i,j) or element (i,j)) to the sum variable. In step 1014, the thread increments index variable j. If, in step 1016, index variable i is not equal to index variable j, then the method proceeds to step 1012.

Returning to step 1016, if index variable i is equal to index variable j, then the method proceeds to step 1020, where the thread increments index variable i. In step 1022, the thread adds an inverse of the contents of cell (i,j) to the sum variable. An inverse is used because each cell at this point is actually a matching inverse with respect to the sum being computed. If, in step 1024, index variable i is not equal to a maximum value then the method proceeds to step 1020. The maximum value corresponds to N, where N defines how many atoms are included in the force matrix.

Returning to step 1024, if index variable i is equal to the maximum value, then them method terminates in step 1030, where the thread stores the contents of the sum variable (a final sum) in the output buffer.

In sum, a method for efficiently computing a force matrix of inter-atomic forces and net forces for each atom is disclosed. The inter-atomic forces are represented by a force matrix, which is partitioned into tiles for processing. Each tile is assigned to a thread group, which computes inter-atomic forces for the cells of the tile. A tile that includes no diagonal cells is an off-diagonal tile, while a tile that includes diagonal cells is an on-diagonal tile. Each cell of an on-diagonal tile needs to be computed, while only an upper set of cells need to be computed for an on-diagonal tile. Cells within a given tile are selected for inter-atomic force computation according to one of three methods. In a first method, each row of a tile is assigned to a thread for processing. Each thread initially processes a cell along a horizontal axis selected according to a thread index, which provides an offset to each thread. The offset yields and access pattern that avoids access conflicts to a GRF. After an initial processing step, each thread increments (with wrapping on tile boundaries) the offset and processes a subsequent cell. After each cell within a horizontal row of the tile is processed, the thread terminates. The first method may be used with on-diagonal and off-diagonal tiles. In a second method, applicable to on-diagonal tiles, the first method is modified such that the horizontal offset is set to a constant for each thread.

A set of reduction sum operations is executed on the force matrix to generate a net force for atoms represented in the force matrix. Each reduction operation may be assigned to a thread for processing. Each thread adds force components along one axis of the force matrix and subsequently adds force components along a second axis of the force matrix.

One advantage of the invention is improved computational efficiency gained through more efficient memory access patterns and more efficiency use of computing resources within the parallel processing unit.

A second advantage of the invention is that, through efficiency, system resources are freed up for other computations. For example, additional computation kernels may be able to execute concurrently with kernels executing steps 814 and 818 of FIG. 8, providing greater overall system efficiency.

One embodiment of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

The invention has been described above with reference to specific embodiments. Persons skilled in the art, however, will understand that various modifications and changes may be made thereto without departing from the broader spirit and scope of the invention as set forth in the appended claims. The foregoing description and drawings are, accordingly, to be regarded in an illustrative rather than a restrictive sense.

What is claimed is:

1. A computer-implemented method for computing net forces on atoms in a protein, the method comprising:

instantiating a first thread group via at least one parallel processing unit to compute net forces for a plurality of atoms represented in a force matrix, wherein each column of the force matrix corresponds to a different atom in the protein, and each row of the force matrix corresponds to a different atom in the protein, and values of non-diagonal cells in the force matrix represent inter-atom forces between different atoms in the protein;

for each thread in the first thread group, identifying a cell in the force matrix corresponding to the value of a first index variable associated with the thread and a value of a second index variable associated with the thread, wherein each value of the first index variable represents a different atom represented in the force matrix, and each value of the second index variable represents a different atom in the force matrix;

for each thread in the first thread group, adding the value of the identified cell to a sum variable associated with the thread; and for each thread in the first thread group, storing the value of the sum variable associated with the thread in a memory space.

2. The method of claim 1, for each thread in the first thread group, further comprising the step of initializing a sum variable associated with the thread, a first index variable associated with the thread, and a second index variable associated with the thread.

3. The method of claim 2, wherein the first index values associated with the threads in the first thread group are initialized to values that are offset from one another.

4. The method of claim 3, wherein, for each thread in the first thread group, the value of the first index variable associated with the thread is held equal to the initialized value, and further comprising the steps of incrementing the value of the second index variable associated with the thread, identifying another cell in the force matrix corresponding to the value of the first index variable associated with the thread and the value of the second index variable associated with the thread, and adding the value of the value of the another cell to the sum variable associated with the thread.

5. The method of claim 4, wherein, for each thread in the first thread group, the steps of incrementing the value of the second index variable, identifying another cell in the force matrix, and adding the value of the another cell to the sum variable are repeated until the value of the second index variable associated with the thread is equal to the value of the first index variable associated with the thread.

6. The method of claim 5, wherein, for each thread in the first thread group, the value of the second index variable associated with the thread is held equal to the initialized value of the first index variable associated with the thread, and further comprising the steps of incrementing the value of the first index variable associated with the thread, identifying another cell in the force matrix corresponding to the value of the first index variable associated with the thread and the value of the second index variable associated with the thread, and adding an inverse of the value of the another cell to the sum variable associated with the thread.

7. The method of claim 6, wherein, for each thread in the first thread group, the steps of incrementing the value of the first index variable, identifying another cell in the force matrix, and adding the inverse of the value of the another cell to the sum variable are repeated until the value of the first index variable associated with the thread is equal to the total number of atoms represented in the force matrix.

8. The method of claim 1, wherein the memory space is included within a global register file memory arbitrarily accessible by all threads in the first thread group.

9. The method of claim 8, wherein each thread in the first thread group can write data to any region within the global register file memory.

10. The method of claim 8, wherein the memory space comprises an output buffer having a different slot for each atom represented in the force matrix, and each thread in the first thread group writes the value of the sum variable associated with the thread to a different slot in the output buffer.

11. The method of claim 1, wherein the memory space is included in one or more local register file memories, the first thread group has access to only one of the one or more local register file memories, and each thread in the first thread group has access to only one region within the one local register file memory to which the first thread group has access.

12. A non-transitory computer-readable medium including instructions that, when executed by a processing unit, cause the processing unit to compute net forces on atoms in a protein, by performing the step of:

instantiating a first thread group to compute net forces for a plurality of atoms represented in a force matrix, wherein each column of the force matrix corresponds to a different atom in the protein, and each row of the force matrix corresponds to a different atom in the protein, and values of non-diagonal cells in the force matrix represent inter-atom forces between different atoms in the protein;

for each thread in the first thread group, identifying a cell in the force matrix corresponding to the value of a first index variable associated with the thread and a value of a second index variable associated with the thread, wherein each value of the first index variable represents a different atom represented in the force matrix, and each value of the second index variable represents a different atom in the force matrix;

for each thread in the first thread group, adding the value of the identified cell to a sum variable associated with the thread; and for each thread in the first thread group, storing the value of the sum variable associated with the thread in a memory space.

13. The non-transitory computer-readable medium of claim 12, for each thread in the first thread group, further comprising the step of initializing a sum variable associated with the thread, a first index variable associated with the thread, and a second index variable associated with the thread, wherein the first index values associated with the threads in the first thread group are initialized to values that are offset from one another.

14. The non-transitory computer-readable medium of claim 13, wherein, for each thread in the first thread group, the value of the first index variable associated with the thread is held equal to the initialized value, and further comprising the steps of incrementing the value of the second index variable associated with the thread, identifying another cell in the force matrix corresponding to the value of the first index variable associated with the thread and the value of the second index variable associated with the thread, and adding the value of the value of the another cell to the sum variable associated with the thread.

15. The non-transitory computer-readable medium of claim 14, wherein, for each thread in the first thread group, the steps of incrementing the value of the second index variable, identifying another cell in the force matrix, and adding the value of the another cell to the sum variable are repeated until the value of the second index variable associated with the thread is equal to the value of the first index variable associated with the thread.

16. The non-transitory computer-readable medium of claim 15, wherein, for each thread in the first thread group, the value of the second index variable associated with the thread is held equal to the initialized value of the first index variable associated with the thread, and further comprising the steps of incrementing the value of the first index variable associated with the thread, identifying another cell in the force matrix corresponding to the value of the first index variable associated with the thread and the value of the second index variable associated with the thread, and adding an inverse of the value of the another cell to the sum variable associated with the thread.

17. The non-transitory computer-readable medium of claim 16, wherein, for each thread in the first thread group, the steps of incrementing the value of the first index variable, identifying another cell in the force matrix, and adding the inverse of the value of the another cell to the sum variable are repeated until the value of the first index variable associated with the thread is equal to the total number of atoms represented in the force matrix.

18. The non-transitory computer-readable medium of claim 12, wherein the memory space is included within a global register file memory arbitrarily accessible by all threads in the first thread group.

19. The non-transitory computer-readable medium of claim 18, wherein the memory space comprises an output buffer having a different slot for each atom represented in the force matrix, and each thread in the first thread group writes the value of the sum variable associated with the thread to a different slot in the output buffer.

20. The computer-readable medium of claim 12, wherein the memory space is included in one or more local register file memories, the first thread group has access to only one of the one or more local register file memories, and each thread in the first thread group has access to only one region within the one local register file memory to which the first thread group has access.

21. A computing device, comprising:
a system memory; and
a parallel processing unit coupled to the system memory and including one or more processing cores, wherein one or more thread groups executes within each processing core, the one or more processing cores are coupled to a global register file memory that is arbitrarily accessible by each thread in the one or more thread groups, and the parallel processing unit is configured to:
instantiate a first thread group to compute net forces for a plurality of atoms represented in a force matrix, wherein the force matrix resides in a portion of the global register file memory, each column of the force matrix corresponds to a different atom in the protein, and each row of the force matrix corresponds to a different atom in the protein, and values of non-diagonal cells in the force matrix represent inter-atom forces between different atoms in the protein,
for each thread in the first thread group, identify a cell in the force matrix corresponding to the value of a first index variable associated with the thread and a value of a second index variable associated with the thread, wherein each value of the first index variable represents a different atom represented in the force matrix, and each value of the second index variable represents a different atom in the force matrix,
for each thread in the first thread group, add the value of the identified cell to a sum variable associated with the thread, and
for each thread in the first thread group, store the value of the sum variable associated with the thread in a memory space.

* * * * *